United States Patent [19]
Greenberger et al.

[11] Patent Number: 5,766,950
[45] Date of Patent: Jun. 16, 1998

[54] EXPANSION OF BONE MARROW STROMAL CELLS

[75] Inventors: Joel S. Greenberger, Sewickley, Pa.; David R. Hurwitz, Acton, Mass.

[73] Assignee: ALG Company, Marlborough, Mass.

[21] Appl. No.: 581,059

[22] Filed: Dec. 29, 1995

[51] Int. Cl.$^6$ .............................. C12N 5/02; C12N 5/06; A61K 38/18; A61K 38/39
[52] U.S. Cl. .................... 435/397; 435/402; 435/405; 435/372; 530/354; 530/399
[58] Field of Search .................... 435/240.2, 240.21, 435/240.23, 240.243, 397, 372, 402, 405; 530/354, 399

[56] References Cited

U.S. PATENT DOCUMENTS

| | | | |
|---|---|---|---|
| 5,198,356 | 3/1993 | Lieberman et al. | 435/240.2 |
| 5,256,560 | 10/1993 | Lawman et al. | 435/240.2 |
| 5,324,656 | 6/1994 | Ham et al. | 435/240.2 |
| 5,328,844 | 7/1994 | Moore | 435/240.31 |
| 5,399,493 | 3/1995 | Emerson et al. | |
| 5,408,041 | 4/1995 | Mundy et al. | 530/413 |
| 5,453,357 | 9/1995 | Hogan | 435/7.21 |
| 5,460,964 | 10/1995 | McGlave et al. | 435/240.21 |
| 5,474,687 | 12/1995 | Van Vlasselaer | 210/782 |
| 5,486,459 | 1/1996 | Caplan et al. | 424/93.7 |

FOREIGN PATENT DOCUMENTS

| | | |
|---|---|---|
| WO 90/15877 | 12/1990 | WIPO. |
| WO 91/18620 | 12/1991 | WIPO. |
| WO 95/02040 | 1/1995 | WIPO. |
| PCT/US95/17073 | 12/1995 | WIPO. |

OTHER PUBLICATIONS

Zhang, L. et al. J. Cell Science. 108(1): 323–331, Jan. 1995.
Harlow, E. and Lane, D. eds. in Antibodies: A Laboratory Manual. Cold Spring Harbor Laboratory. New York. pp. 250–251, 1988.
Hirano, H et al. Clinical Orthopaedics and Related Research. 154:234–248, Jan. 1981.
Brunner et al., 1993, Blood 81:631–638.
Burgess et al., 1989, Ann. Rev. Biochem. 58:575–606.
Dionne et al., 1991, Ann. N.Y. Acad. Sci. 638:161–166.
Dooley et al., 1995, J. Cell. Physiol. 165:386–397.
Dorshkind, 1980, Ann. Rev. Immunol. 8:111–137.
Gartner et al., 1980, Proc. Natl. Acad. Sci. USA 77:4756–4759.
Hauser et al., 1995, J. Histochem. Cytochem. 43;371–379.
Haynesworth et al., 1992, Bone 13:81–88.
Selden et al., 1986, Mol. Cell. Biol. 6:3173–3179.
Sorger et al., 1995, In Vitro Cell. Dev. Biol.—Animal 31:671–683.
Thomas, 1987, FASEB J. 1:434–440.
Thomson et al., 1993, Bone & Mineral Research 8:1173–1183.
SIGMA 1994 Catalogue & Price List.

*Primary Examiner*—David Saunders
*Assistant Examiner*—F. Pierre VanderVegt
*Attorney, Agent, or Firm*—Fish & Richardson P.C.

[57] ABSTRACT

The invention features a method for the selection and expansion of bone marrow stromal cells. The method includes the steps of obtaining bone marrow stromal cells; introducing the stromal cells into a vessel pre-coated on an inner surface with a gelatin, and containing a culture medium including an acidic fibroblast growth factor ("aFGF") polypeptide; and expanding the stromal cells in the culture medium under conditions and for a time sufficient to obtain an increased number of bone marrow stromal cells. The culture medium additionally can include heparin, and the vessel additionally can be precoated with fetal bovine serum.

22 Claims, 3 Drawing Sheets

EXPANSION OF BONE MARROW STROMAL CELLS

BACKGROUND OF THE INVENTION

This invention relates to culturing bone marrow stromal cells.

Bone marrow is a complex and dynamic organ system comprised of hematopoietic cells, bone marrow stromal cells, and extracellular matrix. Pluripotent stem cells within the bone marrow proliferate and differentiate into numerous cell types including erythrocytes and leukocytes. It has been known for some time that association between stem cells and stromal cells is critical for this process. Studies in cell culture have shown that a layer of adherent stromal cells must be established before hematopoietic stem cells can grow and differentiate.

Bone marrow stromal cells are a heterogeneous population of cells that are defined by their morphology and function. In cell culture, they have a characteristic spindle-shaped morphology and secrete growth factors and components that form the extracellular matrix. Stromal cells have been shown to divide in culture in response to epidermal growth factor (EGF; Kimura et al., 1988, Br. J. Hematol. 69:9–12), platelet derived growth factor (PDGF; Kimura et al., supra), and basic fibroblast growth factor (bFGF; Kimura et al., supra; Oliver et al., 1990, Growth Factors, 3:231–236).

The discovery of fibroblast growth factors was based on observations many years ago that extracts from brain could stimulate the division of fibroblasts (see Thomas, 1987, FASEB J., 1:434–440). Particular FGFs have since been isolated and this family now contains at least seven members, including acidic and basic FGF (aFGF and bFGF). These two factors are encoded by different single copy genes and are only 55% identical at the amino acid level (Thomas, supra).

As is the case for most growth factors, FGFs exert their mitogenic activity by binding to cell surface receptors. Currently, four related FGF receptors (FGFR1–FGFR4) have been identified. Each of the FGF receptors exist in multiple forms and the relative affinity of aFGF and bFGF varies for each receptor form (reviewed in Burgess et al., 1989, Ann. Rev. Biochem, 58:575–606; Dionne et al., 1991, Ann. N.Y. Acad. Sci, 638:161–166; Johnson et al., 1993, Adv. Cancer Res. 60:1–41). Basic- and acidic FGF also differ in their response to heparin. In cell culture, heparin complexes with both FGFs, but substantially augments only the mitogenic activity of aFGF (Thomas, supra).

Bone marrow transplantation or implantation is a promising therapy for a number of diseases that involve hematopoietic cells. Transplantation can serve to replace cells that have been damaged by an intrinsic disease, such as an anemia, or in instances where hematopoietic cells have been destroyed by chemotherapy or radiation therapy. Transplantations can be autologous, i.e., the patient can serve as his or her own donor. Alternatively, a patient could receive bone marrow from a histocompatible donor. To date, however, conditions for culturing bone marrow, particularly bone marrow stromal cells, which could be transplanted and used in numerous gene therapies, have not been optimized. A major obstacle to gene therapies that are based on the modification of stromal cells is the procurement of therapeutically useful numbers of stromal cells. Consequently, despite the success of bone marrow transplantation, gene therapies that require successful transplantation of bone marrow stromal cells have not yet been realized.

SUMMARY OF THE INVENTION

The invention is a novel method for culturing bone marrow stromal cells, and is based on the discovery that acidic FGF (aFGF), or a combination of aFGF and heparin, significantly enhances the establishment and subsequent expansion of bone marrow stromal cells. By employing this method, bone marrow stromal cells can be expanded in culture to previously unprecedented levels that are clearly beneficial for therapeutic uses. Thus, this culturing method allows bone marrow stromal cells to be used in many types of gene therapies.

In general, the invention features a method for the expansion of bone marrow stromal cells to obtain a total of at least $10^7$, and preferably more than $10^9$, bone marrow stromal cells. The method includes the steps of: (a) obtaining bone marrow stromal cells, e.g., from a bone marrow aspirate; (b) introducing the stromal cells into a vessel pre-coated on an inner surface with a gelatin, e.g., 1.0 percent gelatin in water, and containing a culture medium including an acidic fibroblast growth factor ("aFGF") polypeptide; and (c) expanding the stromal cells in the culture medium under conditions and for a time sufficient to obtain an increased number of bone marrow stromal cells. In this method, the culture medium further preferably includes at least 0.05 units/ml of heparin. The inner surface of the vessel additionally can be precoated with fetal bovine serum prior to introducing the bone marrow stromal cells.

In particular, the culture medium can include 1.0 to 50.0 percent by volume fetal bovine serum, 0.01 to 100.0 ng/ml aFGF polypeptide, and 0.05 to 100 units/ml heparin. In a specific embodiment, the culture medium includes 16.0 percent by volume fetal bovine serum, 1.0 ng/ml aFGF polypeptide, and 5.0 units/ml heparin.

In a preferred aspect of the invention, the expansion step (c) includes the steps of: (i) removing culture medium and non-adherent cells from the vessel; (ii) adding an amount of fresh culture medium to the vessel; (iii) removing culture medium and non-adherent cells from the vessel and centrifuging the medium and non-adherent cells to form a pellet of non-adherent cells; (iv) resuspending the pellet of non-adherent cells in an amount of culture medium taken from the vessel to form a non-adherent cell mixture; and (v) returning the non-adherent cell mixture to the vessel. In this method, the amounts of fresh culture medium in step (ii) and culture medium taken from the vessel to resuspend the pellet of non-adherent cells in step (iv) can be equal. In particular, step (i) can be performed after stromal cells have adhered to the inner surface of the vessel, and steps (ii) and (iii) can be performed about one week after step (i).

In each of these methods, the bone marrow stromal cells can be fresh stromal cells obtained from primary aspirates of bone marrow from a vertebrate, e.g., a mammal, living or not, or can be obtained from bones removed from a vertebrate, e.g., a human, non-human primate, cow, dog, pig, or other animal. The bone marrow stromal cells also can be obtained from a bone marrow stromal cell culture or from a frozen stock of bone marrow stromal cells.

The invention also features a complete bone marrow stromal cell medium including greater than 12.5 percent by volume fetal bovine serum, an acidic fibroblast growth factor ("aFGF") polypeptide, and a heparin polypeptide. In particular, the medium can include 12.6 to 50 percent by volume fetal bovine serum, 0.01 to 100.0 ng/ml aFGF polypeptide, and 0.05 to 100 units/ml heparin. In a specific embodiment, the medium includes 16 percent by volume fetal bovine serum, 1.0 ng/ml aFGF, and 5.0 units/ml heparin. The medium can further include a fungicide, e.g., FUNGIZONE™ (amphotericin B) at a concentration of 25 µg/ml, and one or more antibiotics, e.g., 25 µg/ml gentamicin, 100 units/ml penicillin, and 100 µg/ml streptomycin sulfate.

In another aspect, the invention features a kit for the selection and expansion of bone marrow stromal cells. The kit includes one or more culture vessels coated on an inner surface with a gelatin, e.g., 1.0 percent gelatin in water, and a bone marrow stromal cell medium including an aFGF polypeptide and heparin. The medium can be a liquid or a lyophilized powder, and can be provided within the vessel or separately.

As used herein, an "aFGF polypeptide" is any polypeptide that has an amino acid sequence that is the same as, or substantially identical to, all or a portion of the naturally occurring aFGF protein and which has substantially the same function as the natural or full-length recombinant aFGF as described herein with respect to bone marrow stromal cells. Thus, the term includes recombinant aFGF (e.g., manufactured by Life Technologies, Inc., Grand Island, N.Y.; #13241-013), "aFGF analogues," i.e., mutant forms of aFGF, and natural or synthetic polypeptide fragments of the full-length aFGF protein and analogues, as long as these analogues and fragments have substantially the same function as natural or full-length recombinant aFGF with respect to bone marrow stromal cells as described herein. These analogues and fragments can easily be tested for their function by using the culture methods described below. Acidic FGF analogues and fragments that do not provide at least $10^7$ cells with these methods are not within the present invention.

Similarly, "heparin" is any glycosaminoglycan that has a repeating disaccharide sequence that is the same as, or substantially identical to, the repeating disaccharide sequence of naturally occurring heparin and which has substantially the same function as natural heparin, as described herein, with respect to bone marrow stromal cells. Thus, the term includes natural heparin, chemically modified natural heparin, e.g., sodium heparin (ElkinsSinn, Inc., Cherry Hill, N.J.), or synthetic heparin, as long as they have substantially the same function as natural heparin with respect to bone marrow stromal cells as described herein. The heparin function can be assayed using the culture methods described below.

By "polypeptide" is meant any chain of amino acids, regardless of length or post-translational modification, e.g., glycosylation, phosphorylation, or chemical modification, and thus includes natural and synthetic peptides and proteins.

By "mutant form" of aFGF is meant a polypeptide that includes any change in the amino acid sequence compared to the naturally occurring protein, as long as the mutant form has substantially the same function as the natural or full-length recombinant protein as described herein with respect to bone marrow stromal cells. These changes can arise, e.g., spontaneously by chemical energy, e.g., X-ray, or by other forms of mutagenesis, by genetic engineering, or as a result of mating or other forms of exchange of genetic information encoding the aFGF polypeptide. Mutations can include, for example, substitutions, deletions, insertions, inversions, translocations, or duplications. The mutations are preferably conservative substitutions, e.g., substitutions within the following groups: glycine alanine; valine, isoleucine, leucine; aspartic acid, glutamic acid, asparagine, glutamine; serine, threonine; lysine, arginine; and phenylalanine, tyrosine.

The term "identical" as used herein in reference to polypeptides, refers to the amino acid sequence similarity between two polypeptides. When an amino acid position in both of the polypeptides is occupied by identical amino acids, then they are identical at that position. Thus, by "substantially identical" is meant an amino acid sequence that is at least 80%, preferably 85%, more preferably 90%, and most preferably 95% identical to a reference amino acid sequence, and which retains the same functional activity as the reference sequence. Identity of amino acid sequences is typically measured using sequence analysis software (e.g., Sequence Analysis Software Package of the Genetics Computer Group, University of Wisconsin Biotechnology Center, 1710 University Avenue, Madison, Wis. 53705).

As used herein, "expansion" or "expanding" of cells means culturing cells for a time and under conditions that allow the cells not only to grow and thrive, but to multiply to obtain a greater number of cells at the end of the expansion than at the beginning of the expansion.

As used herein, a "passage" is the process whereby cells that have reached a given number, or a given density, up to and including and beyond confluence, are detached from the tissue culture vessel, collected in an aggregate, such as a pellet formed by centrifugation, and resuspended in tissue culture medium. The suspension is then distributed to tissue culture vessels, such as plates or flasks, in such a way as to provide the cells with a greater total surface area on which to grow and divide than they had access to previously. This may be done by increasing the number of vessels. For example, the cells growing in one vessel may be detached, collected, resuspended, and distributed to two or more vessels. This process also includes providing the cells with a volume of tissue culture medium that supports cellular growth and division.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
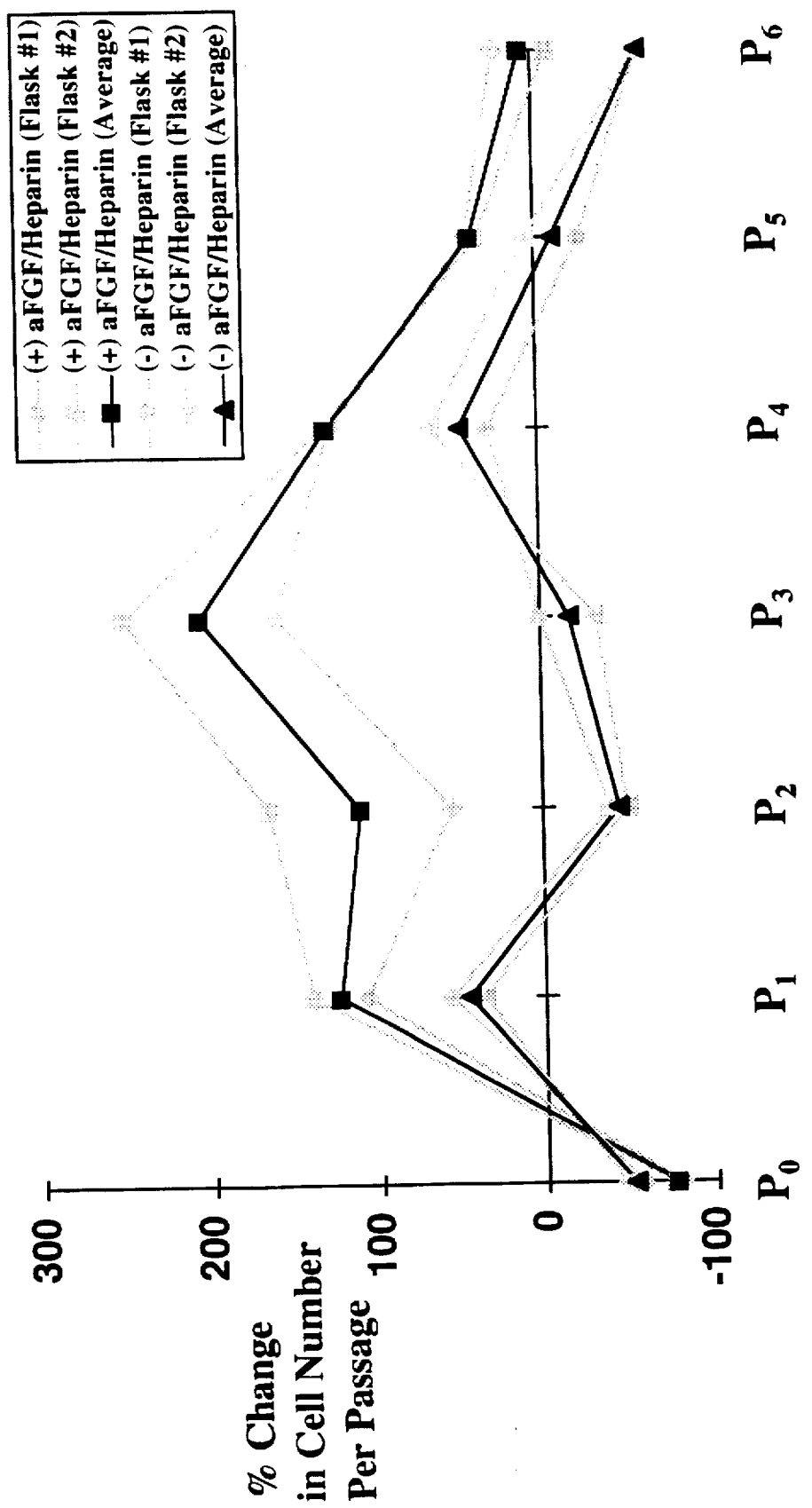
FIG. 1 is a graph depicting the growth of bone marrow stromal cells cultured in the presence or absence of aFGF and heparin. Growth is measured in terms of the percentage change in cell number per passage.

To develop cultures of bone marrow stromal cells that can be used for transplantation, bone marrow was obtained from humans or dogs and grown in specially prepared tissue culture flasks. In addition, the medium was modified with acidic fibroblast growth factor (aFGF) and heparin and was renewed according to a particular regimen. Using this novel method, a large number of bone marrow stromal cells were established in culture and expanded to yield an unprecedented number of cells, which would be required for effective gene therapy with stromal cells.

There now follows a description of the method for culturing bone marrow stromal cells as well as a description of the secretion of human growth hormone (hGH) by transfected canine bone marrow stromal cells in vitro.

Method of Culturing Canine Bone Marrow Stromal Cells

Dogs were fully anesthetized and whole bone marrow was aspirated aseptically from the iliac crest. The aspirate syringes contained heparin to prevent clotting. The bone marrow was transferred from the syringe to a 50 ml conical tube containing 15 mls of a chilled tissue culture medium, such as RPMI or DMEM, containing anti-fungal and anti-biotic agents (50 µg/ml FUNGIZONE™ (amphotericin B); 50 µg/ml gentamicin; 100 units/ml penicillin; 100 µg/ml streptomycin sulfate). Approximately 10–15 mls of bone marrow aspirate was added to each tube of medium and the mixture was kept on ice.

Nucleated cells were prepared from the bone marrow samples by standard Ficoll cushion technique. Briefly, 15 ml of FICOLL-PAQUE™ (Pharmacia Biotech) was placed in a 50 ml conical tube and one half of each of the marrow-medium samples was carefully layered on top of the Ficoll. The samples were centrifuged at 400×g for 30 minutes at 18° C. with the brake off so that the centrifuge head decelerated slowly after the elapsed time. The top layer of the resultant preparation, which contained cell-free medium, was removed and discarded. The middle layer, which contained nucleated cells, was carefully collected and placed into a fresh 50 ml tube containing 20 ml of tissue culture medium, as described above. Additional medium was added to bring the final volume to 50 ml.

The nucleated cells include the bone marrow stromal cells. However, the stromal cells represent only a small fraction, i.e., about one in one thousand, of the total number of nucleated bone marrow cells obtained in a bone marrow aspirate.

The nucleated cells were collected in a pellet by centrifugation at 100×g for 10 minutes. The cell pellet was washed with tissue culture medium (RPMI or DMEM with FUNGIZONE™ (amphotericin B) (25 µg/ml), gentamicin (25 µg/ml), penicillin (100 units/ml) and streptomycin sulfate (100 µg/ml)), and resuspended in 5–10 ml of "complete bone marrow stromal cell medium" ("complete medium"). After resuspension the cells were counted.

Generally, the complete bone marrow stromal medium contains the following ingredients in the following ranges of amounts or concentrations. DMEM with 1 to 50% fetal bovine serum (FBS) (preferably greater than 12.5%); 0.01 to 100 ng/ml of an aFGF polypeptide, e.g., recombinant aFGF; 0.05 to 100 units/ml of a heparin polypeptide, e.g., sodium heparin; 0.25 to 250 µg/ml of FUNGIZONE™ (amphotericin B) ; 0.25 to 250 µg/ml of gentamicin; 1 to 1000 units/ml penicillin; and 1 to 1000 µg/ml of streptomycin sulfate. As used in the experiments described below, the complete medium contained DMEM with 16 percent by volume heat-inactivated FBS, aFGF (1 ng/ml), heparin (5 units/ml), FUNGIZONE™ (amphotericin B) -(25 µg/ml), gentamicin (25 µg/ml), penicillin (100 units/ml), and streptomycin sulfate (100 µg/ml).

Tissue culture flasks (T150 $cm^2$) are preferably coated initially with gelatin and FBS. Specifically, a solution of gelatin (Sigma; 1% in water) was added to each flask until the bottom of the flask was just covered. The excess was removed and the flasks were left undisturbed, bottom side down, at room temperature for at least 30 minutes. The flasks can be refrigerated at this point for later use. Heat-inactivated FBS was then added to the gelatinized flasks. As before, the excess solution was removed and the flasks were left, bottom side down, at room temperature for at least 30 minutes. The flasks can be used at this point or refrigerated.

The nucleated cells of the bone marrow, prepared as described above, were added to the prepared flasks at approximately $1 \times 10^8$ cells/T150 flask. The cells were incubated in 15 mls of complete bone marrow medium, at 33° C., in the presence of 5% $CO_2$. After 3–4 days, or when the stromal cells have adhered to the inner surface of the tissue culture vessel, 15 ml of fresh complete medium was added to the cultures, dropwise, so the cells were not disturbed. One week later, before vital components within the medium are depleted, the so-called "conditioned medium," i.e., the medium in the flask which contains non-adherent cells, was removed, and 15 ml of fresh complete medium was added to the flask. The non-adherent cells were pelleted by centrifugation at 500×g for 5 minutes, resuspended in 15 ml of conditioned medium and returned to the original flask. Thus, the non-adherent cells were returned to the flask and the medium was changed in such a way that it contained one part fresh medium and one part conditioned medium.

In general, the key to this regimen of cell culture is to: (1) coat the inner surface of the tissue culture vessel with a solution of gelatin, (2) keep returning the non-adherent cells to the culture when exchanging the medium, (3) add medium that contains sufficient nutrients to sustain growth without removing all of the substances secreted by the bone marrow cells, which enhance their growth, (4) supplement the tissue culture medium with aFGF, and (5) supplement the tissue culture medium with heparin.

This process, where the non-adherent cells are removed, pelleted, and returned to the culture with equal parts of fresh and conditioned medium, is repeated once a week, for 2 to 3 weeks, or until a monolayer of adherent cells has formed. Once the monolayer of bone marrow stromal cells developed, the cells were passaged by splitting them 1:2 or 1:3 into fresh flasks. At this point, and from this point on, the flasks for additional passages were coated with gelatin, but not with FBS. It is also no longer necessary to feed the established stromal cells with conditioned medium or to return non-adherent cells to the culture. The cells can be passaged in this manner at least 8 times or more.

This method can be used to select and expand canine or human (or other vertebrate) bone marrow stromal cells, to develop a total cell number of more than $10^8$, and even more than $3 \times 10^9$ in vitro, from bone aspirates of individual subjects. Other techniques for obtaining bone marrow can also be used. The bone marrow stromal cells obtained from dogs by this method exhibit the characteristic appearance of fibroblast-like bone marrow stromal cells. Given that the success of gene therapy depends on the cellular production of adequate levels of the transgene product, which can be quite low, the ability to expand stromal cells in culture to $10^8$ to $10^9$ or more represents a substantial improvement.

Although stromal cells from primary canine bone marrow aspirates could establish themselves in culture at P0 (Passage 0), whether or not aFGF and heparin were present, only cells grown in the presence of these two factors continued to grow well after the first or second passage. In addition, the cells grown with aFGF and heparin maintained the fibroblast-like stromal cell morphology longer than stromal cells grown without these factors.

Example

Iliac crest bone marrow aspirates were prepared as described from a dog designated ALG-5, and divided into two portions so that half of the cells could be grown with aFGF and heparin, and the other half could be grown without. Tissue culture flasks were seeded with $2.75 \times 10^7$ primary bone marrow cells and cultured by the methods described above, where stromal cell-conditioned medium and non-adherent cells were returned to the flasks at the first passage. When all flasks contained a confluent layer of stromal cells, the cells were trypsinized and T75 flasks (passage 1, P1) were seeded with $2.5 \times 10^6$ cells derived from each of the P0 flasks. These cells were harvested one week later, and $2 \times 10^6$ cells from each flask were passaged (P2), still in either the presence or absence of aFGF and heparin.

Similarly, P2 cells were harvested 8 days after seeding, and $1 \times 10^6$ cells were passaged into P3 flasks. The number of cells passaged was reduced at this point because the number of cells cultured in the absence of aFGF and heparin was limiting; only $1 \times 10^6$ cells were available for re-seeding. All flasks were re-seeded with this number of cells so that each flask continued to hold a comparably sized population.

Passage 3 (P3) cells were harvested 8 days after seeding and $1 \times 10^6$ cells were seeded into P4 flasks. The cells continued to be passaged and were counted carefully each time they were harvested and re-seeded. After the fourth passage, the cells that were cultured in the presence of aFGF and heparin reached confluence much more quickly (7 days) than the cells that were grown without these factors (14 days).

By comparing the number of cells obtained when the cells were harvested at the end of each passage with the number of cells seeded into the flasks at the beginning of each passage, a percentage change in cell number was determined. A positive number indicates an increase in cell number, a negative number indicates a decrease in cell number, and a zero value indicates no change in cell number.

Adherent stromal cells were established in all flasks of primary cultures (P0). A higher cell count was found at the end of P0 in flasks lacking aFGF and heparin (FIG. 1). Although both groups of cells expanded during P1, the growth of cells cultured in the presence of aFGF and heparin was 2.5-fold greater than cells grown in the absence of aFGF and heparin. Perhaps more importantly, cells cultured with aFGF and heparin continued to grow in number during passages 2, 3, 4, and 5 while cells cultured without aFGF and heparin grew very poorly or not at all during these passages.

The negative numbers in FIG. 1 for all flasks during P0 reflect the fact that bone marrow stromal cells are only a small fraction of the total population of nucleated cells in the primary bone marrow aspirate, and further demonstrate that aFGF and heparin have significant positive effects on the growth of canine bone marrow stromal cells in vitro.

Figure 2:
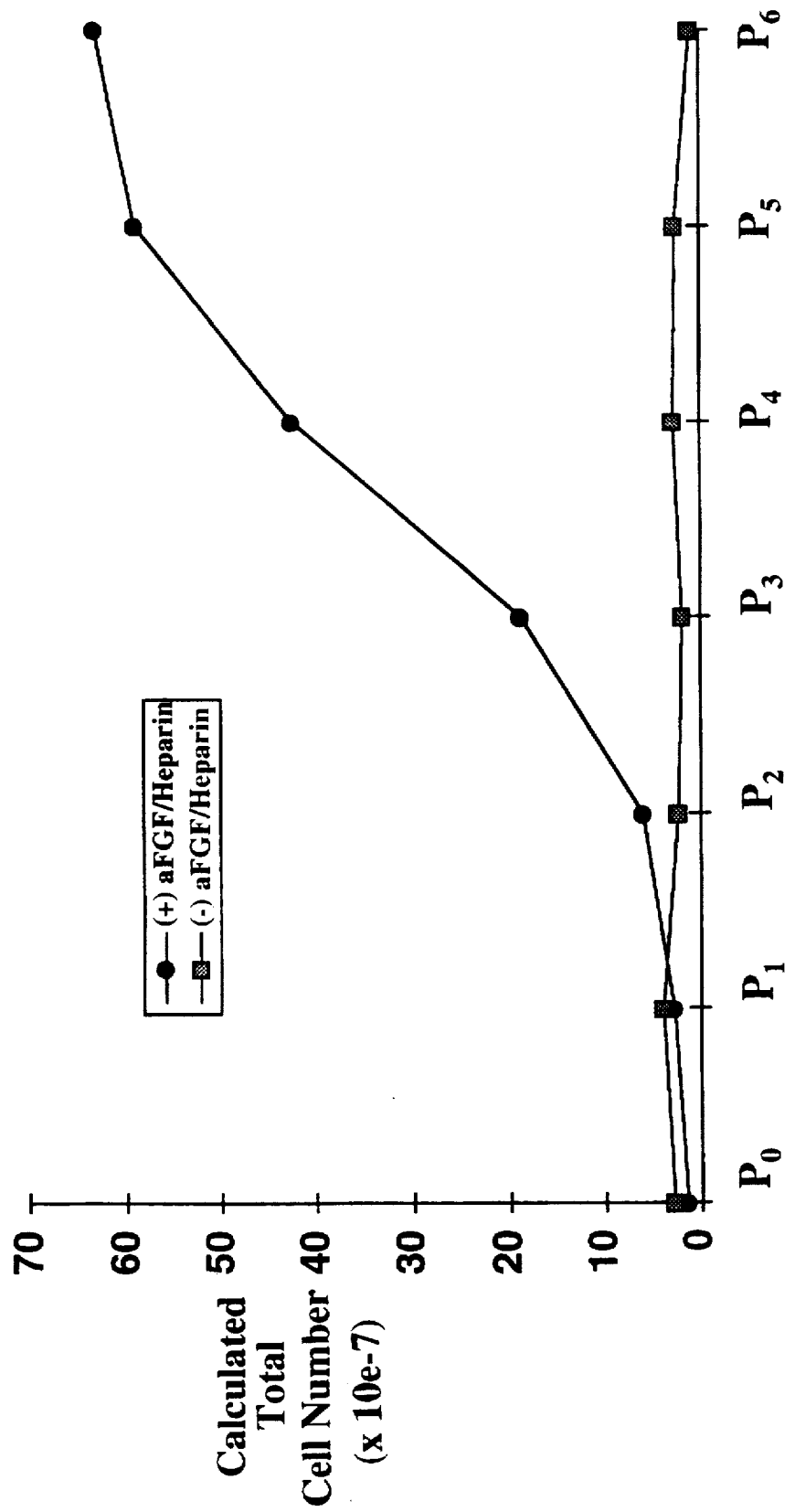
FIG. 2 is a graph depicting the total growth of bone marrow stromal cells cultured in the presence or absence of aFGF and heparin.

The total growth of bone marrow stromal cells obtained from dog ALG-5 was also calculated in the presence and absence of aFGF and heparin. This figure (total growth) was determined by multiplying the total number of stromal cells in each flask (+/− aFGF and heparin) at the end of the period of establishment by the average percentage change in cell number for the first passage. Total growth was similarly calculated for each subsequent passage (FIG. 2). As shown in the graph in FIG. 2, the culture without aFGF and heparin showed essentially no growth. On the other hand, the culture supplemented with aFGF and heparin showed a significant calculated growth to over $60 \times 10^7$ cells by P6.

Cells derived from dog ALG-5 were also inspected visually at the end of each passage, just before they were trypsinized and harvested. The cells grown with aFGF and heparin maintained a fibroblast-like morphology over a number of passages while the cells cultured without aFGF and heparin changed to a flattened morphology after the first or second passage.

Taken together, these results demonstrate that aFGF and heparin clearly enhance the growth of canine bone marrow stromal cells and maintain the characteristic fibroblast-like morphology of these cells in culture.

Method of Culturing Human Bone Marrow Stromal Cells

Human bone marrow was removed from femoral heads that were discarded during hip replacement surgeries. Other techniques for obtaining bone marrow can also be used. The bone marrow was put into tubes containing tissue culture medium, such as RPMI or DMEM containing 50 µg/ml FUNGIZONE™ (amphotericin B) and 50 µg/ml gentamicin. The bone and tissue suspended in the medium were finely minced using sterile scissors, centrifuged at 500×g for 10 minutes and resuspended in tissue culture medium containing 16% heat-inactivated FBS by gently inverting the tube. Larger bone and tissue fragments were then allowed to settle to the bottom of the tube over the course of about 1 minute. The supernatant containing suspended cells was carefully removed and centrifuged at 500×g for 10 minutes. The cell pellet was washed once by centrifugation in complete bone marrow stromal cell medium, resuspended in fresh complete medium, and the cells were counted. These primary bone marrow cells were initially cultured in flasks that were pretreated with gelatin and FBS, as described above for dog bone marrow stromal cell cultures, at $1 \times 10^8$ cells/T150 flask.

Human bone marrow stromal cells were selected and expanded in vitro using the same techniques and complete medium that are described above. In addition, small fragments of the human femoral bones were introduced into prepared tissue culture flasks that contained complete medium. Bone marrow stromal cells grew out of these fragments, adhered to the flasks, and were treated subsequently in the same way as other bone marrow stromal cells. Human bone marrow stromal cells were selected and expanded from primary marrows derived from several individuals and cells were expanded to at least $2 \times 10^8$ cells.

In vitro Expression and Secretion of Human Growth Hormone by Transfected Canine Bone Marrow Stromal Cells To determine whether bone marrow stomal cells that were grown according to the methods described above could be transfected, the plasmid expression vector pETKhGH was prepared and transfected into canine stromal cells using standard techniques. The dog model is an accepted animal model of the human bone marrow system, and results in dog studies are reasonably predictive of efficacy in human patients.

The vector was constructed from plasmid pTKGH (Selden et al., 1986, Mol. Cell Biol., 6:3173–3179), which is comprised of the human growth hormone (hGH) gene, including introns, under the transcriptional regulation of HSV thymidine kinase (TK) promoter sequences (Nichols Institute Diagnostics, San Juan Capistrano, Calif.). In addition, a 179 base pair FokI-PvuII restriction enzyme fragment from the SV40 enhancer was tailed with HindIII sites by PCR using a derivative of the pSV(E)-MLP plasmid (Hurwitz et al., 1987, Nuc. Acids Res. 15:7137–7153) as a template, and cloned into the HindIII site of pTKGH just upstream of the TK promoter. The pETKhGH plasmid lacks a eukaryotic origin of replication and does not integrate into the host cell genome. As such, the vector expresses hGH transiently.

Canine bone marrow stromal cells were transfected with pETKhGH by either the $CaPO_4$-DNA coprecipitation method, using the MBS Mammalian Transfection Kit (Stratagene Cloning Systems, La Jolla, Calif.), or the cationic lipid-DNA complex method using LIPOFECTAMINE® reagent and OPTI-MEM® I reduced-serum medium (Life Technologies) according to the manufacture's instruction. The $CaPO_4$ method was used to transfect cells obtained from dog ALG-3 and the lipofection method was used to transfect cells obtained from dog ALG-9.

DNA was transfected by the $CaPO_4$ method into $3.2 \times 10^6$ cells one day after they were seeded into a T150 flask at P2. The cells were transfected with 150 μg of pETKhGH plasmid for 24 hours. These cells were growing actively and displayed a fibroblast-like morphology.

DNA was transfected by lipofection into $1.2 \times 10^6$ cells one day after they were seeded into a T150 flask at P6. The growth rate of these cells was reduced from that seen in earlier passages and the cellular morphology had changed so that the cells appeared more flattened and spread out. These cells were transfected for six hours with 40 μg of pETKhGH plasmid in a total volume of 4.28 ml of OPTI-MEM® containing 0.24 ml of LIPOFECTAMINE® reagent.

Figure 3:
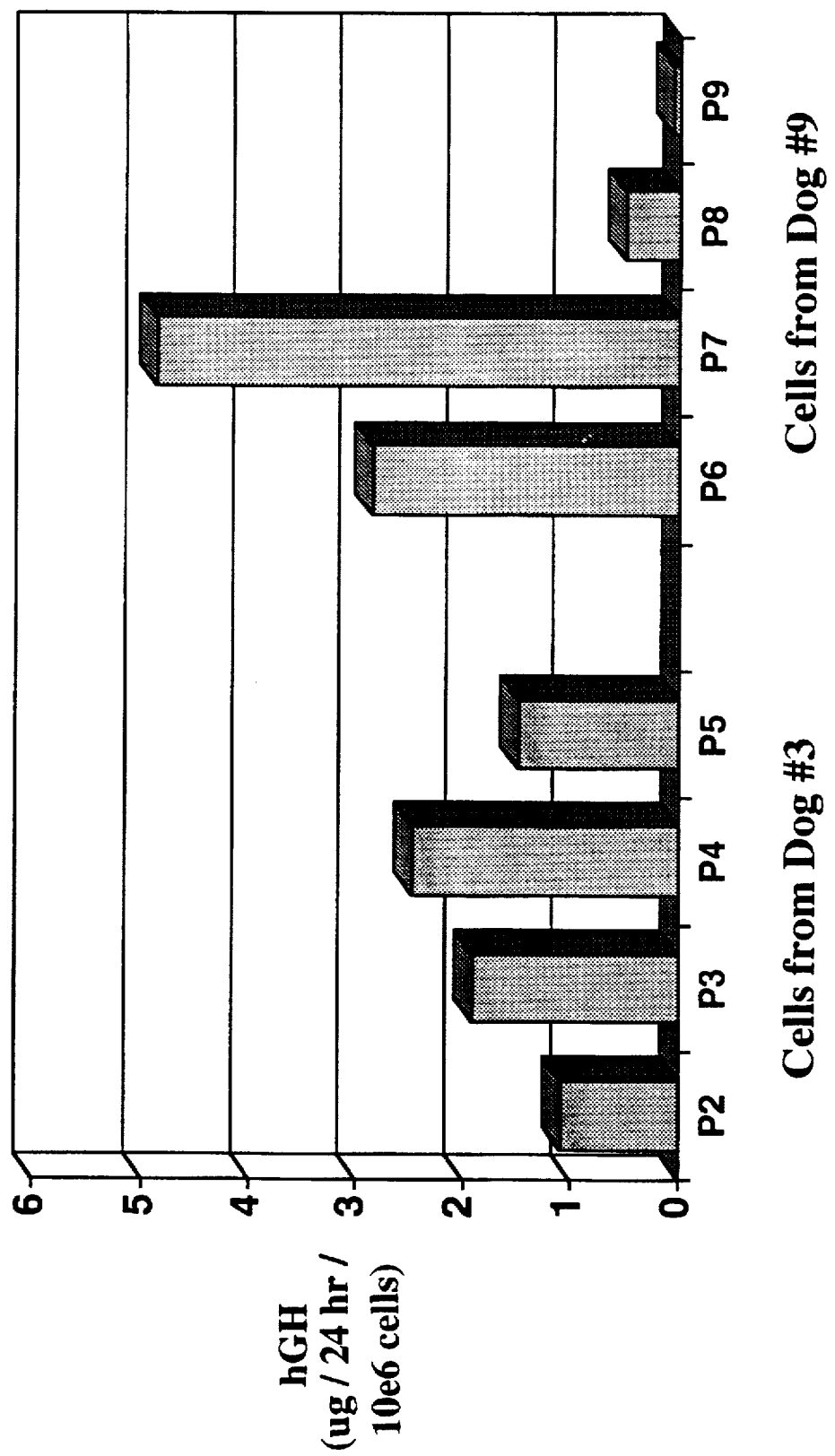
FIG. 3 is a graph depicting the in vitro expression and secretion of human growth hormone (hGH) by transfected canine bone marrow stromal cells.

Levels of hGH secretion were determined by radioimmunoassay (RIA) using hGH-TGES kits (Nichols Institute Diagnostics). The results are expressed as the mean of duplicate measurements. Both early (P2) and late (P6) passage canine stromal cells expressed and secreted high levels of the hGH transgene product after transfection with the expression plasmid pETKhGH (FIG. 3). The absolute levels of hGH expression varied, depending on the individual animal tested, the number of times the cells had been passaged, and the method of transfection.

As shown in FIG. 3, the absolute level of hGH expressed by the cells from dog ALG-3 varied from over 1 to about 2.5 μg/24 hr/$10^6$ cells. The absolute level of hGH expressed by the cells from dog ALG-9 varied from almost 3 to about 5 μg/24 hr/$10^6$ cells from P6 to P7, and then dropped to about 0.5, and then down to almost zero in P8 and P9, respectively.

OTHER EMBODIMENTS

In other embodiments of the invention, bone marrow stromal cells can be cryopreserved either before or after expansion in tissue culture.

To cryopreserve primary aspirates of bone marrow, nucleated cells are prepared using the Ficoll gradient technique described above, and suspended in 50% medium, 50% FBS at a density of, e.g., 2 to $5 \times 10^7$ cells/ml. An amount, e.g., 900 μl, of this suspension is aliquoted into vials, e.g., 2 ml sterile cryogenic vials (Corning #25704), with 100 μl of DMSO. The vials are stored at −80° C. for 24 hours, and then transferred to a −150° C. freezer or to liquid nitrogen tanks for long-term storage.

To cryopreserve stromal cells growing in culture, the media is aspirated from the tissue culture vessel, and the cells are rinsed once with Dulbecco's phosphate buffered saline (Gibco 14190-144). The cells are then detached from the surface of the flask or plate with a solution of trypsin-EDTA (0.05% trypsin, 0.53 mM EDTA; Gibco 25300-062).

The trypsinization is stopped by adding an equal volume of medium, and the cell suspension is centrifuged at 500×g until the cells are pelleted. The pelleted cells are resuspended in medium, e.g., 3 ml, and counted. The cell density is adjusted to $1 \times 10^6$ cells/ml with medium containing 10% dimethyl sulfoxide (DMSO; Sigma D-8779). The cells are aliquoted, e.g., by 1 ml volumes, into sterile cryogenic vials (Corning #25704), and immediately stored at −80° C. overnight. After 24 hours, the vials are transferred to liquid nitrogen tanks or to a -150° C freezer for long-term storage.

Procedures have also been developed to cryopreserve large numbers of cultured stromal cells. For example, after harvesting the cells as described above, 200 ml of cell suspension is placed in a 250 ml centrifuge tube and centrifuged at 500×g in order to pellet the cells. The pelleted cells are resuspended in 10–20 ml of medium and counted. The suspension is then brought to a volume of 45 ml with medium and added to a transfer pack container (Baxter Fenwal, 4R2001) with a sterile syringe fitted with an 18 gauge needle. Five ml of DMSO is then added, and the pack is stored at −80° C. overnight. After 24 hours, the pack is transferred to liquid nitrogen tanks or to a −150° C. freezer for long-term storage. All of these cryopreservation methods can be used for stromal cells from human patients as well as from primates, dogs, cows, and other animals.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A method for the expansion of bone marrow stromal cells, the method comprising:
    (a) introducing bone marrow stromal cells into a vessel pre-coated on an inner surface with a gelatin, and containing a culture medium comprising an acidic fibroblast growth factor ("aFGF") polypeptide; and
    (b) expanding the stromal cells in the culture medium under conditions and for a time sufficient to obtain an increased number of bone marrow stromal cells.

2. The method of claim 1, wherein said culture medium further comprises at least 0.05 units/ml of heparin.

3. The method of claim 2, wherein said culture medium comprises 1.0 to 50.0 percent by volume fetal bovine serum, 0.01 to 100.0 ng/ml aFGF polypeptide, and 0.05 to 100 units/ml heparin.

4. The method of claim 3, wherein said culture medium comprises 16.0 percent by volume fetal bovine serum, 1.0 ng/ml aFGF polypeptide, and 5.0 units/ml heparin.

5. The method of claim 1, wherein said gelatin is 1.0 percent gelatin in water.

6. The method of claim 1, further comprising additionally precoating the inner surface of the vessel with fetal bovine serum prior to introducing the bone marrow stromal cells.

7. The method of claim 1, wherein expanding step (c) comprises the steps of:
    (i) removing culture medium and non-adherent cells from the vessel;
    (ii) adding an amount of fresh culture medium to the vessel;
    (iii) removing culture medium and non-adherent cells from the vessel and centrifuging said medium and non-adherent cells to form a pellet of non-adherent cells;

(iv) resuspending the pellet of non-adherent cells in an amount of culture medium taken from the vessel to form a non-adherent cell mixture; and (v) returning the non-adherent cell mixture to the vessel.

8. The method of claim 7, wherein the amounts of fresh culture medium in step (ii) and culture medium taken from the vessel to resuspend the pellet of non-adherent cells in step (iv) are equal.

9. The method of claim 7, wherein step (i) is performed after stromal cells have adhered to the inner surface of the vessel.

10. The method of claim 7, wherein steps (ii) and (iii) are performed about one week after step (i).

11. The method of claim 1, wherein the bone marrow stromal cells are fresh stromal cells obtained from primary aspirates of bone marrow from a vertebrate.

12. The method of claim 1, wherein the bone marrow stromal cells are obtained from bones removed from a vertebrate.

13. The method of claim 1, wherein the bone marrow stromal cells are obtained from a bone marrow stromal cell culture or from a frozen stock of bone marrow stromal cells.

14. The method of claim 1, wherein the bone marrow stromal cells are mammalian.

15. The method of claim 14, wherein the bone marrow stromal cells are human.

16. The method of claim 14, wherein the bone marrow stromal cells are canine.

17. A complete bone marrow stromal cell medium comprising greater than 12.5 percent by volume fetal bovine serum, an acidic fibroblast growth factor ("aFGF") polypeptide, and heparin.

18. The medium of claim 17, comprising 12.6 to 50 percent by volume fetal bovine serum, 0.01 to 100.0 ng/ml aFGF polypeptide, and 0.05 to 100 units/ml heparin.

19. The medium of claim 17, comprising 16 percent by volume fetal bovine serum, 1.0 ng/ml aFGF, and 5.0 units/ml heparin.

20. The medium of claim 17, further comprising a fungicide and one or more antibiotics.

21. The medium of claim 20, wherein the fungicide is amphotericin B at a concentration of 25 µg/ml, and the one or more antibiotics comprise 25 µg/ml gentamicin, 100 units/ml penicillin, and 100 µg/ml streptomycin sulfate.

22. A kit for the selection and expansion of bone marrow stromal cells, the kit comprising a culture vessel coated on an inner surface with a gelatin and a bone marrow stromal cell medium comprising an aFGF polypeptide and a heparin.

* * * * *